(12) United States Patent
Rieping et al.

(10) Patent No.: US 7,442,530 B2
(45) Date of Patent: Oct. 28, 2008

(54) PROCESS FOR THE PRODUCTION OF L-AMINO ACIDS USING STRAINS OF THE ENTEROBACTERIACEAE FAMILY WHICH CONTAIN AN ENHANCED FADR OR ICLR GENE

(75) Inventors: Mechthild Rieping, Bielefeld (DE); Nicole Siebelt, Rietberg (DE)

(73) Assignee: Evonik Degussa GmbH, Essen (DE)

( * ) Notice: Subject to any disclaimer, the term of this patent is extended or adjusted under 35 U.S.C. 154(b) by 396 days.

(21) Appl. No.: 10/491,893

(22) PCT Filed: Sep. 26, 2002

(86) PCT No.: PCT/EP02/10791

§ 371 (c)(1), (2), (4) Date: Apr. 15, 2004

(87) PCT Pub. No.: WO03/038106

PCT Pub. Date: May 8, 2003

(65) Prior Publication Data

US 2005/0064561 A1    Mar. 24, 2005

(30) Foreign Application Priority Data

Nov. 2, 2001 (DE) ............................... 101 54 102

(51) Int. Cl.
*C12P 13/00* (2006.01)
(52) U.S. Cl. .................................................... 435/115
(58) Field of Classification Search ...................... None
See application file for complete search history.

(56) References Cited

U.S. PATENT DOCUMENTS

2003/0059903 A1* 3/2003 Rieping et al. .............. 435/106

FOREIGN PATENT DOCUMENTS

EP       1 408 123 A1      4/2004

OTHER PUBLICATIONS

Cortay et al (Regulation of the acetate operon in *Escherichia coli*: purification and functional characterization of the IclR repressor, The EMBO Journal vol. 10 No. 3 pp. 675-679, 1991).*
Malumbers et al.(Molecular control Mechanism of lysine and threonine biosynthesis in amino acid-producing Corynebacteria: Redirecting carbon flow FEMS Microbiology Letters 143 (1996) 103-114).*

Gui L et al: "Regulated expression of a repressor protein: FadR activates iclR." Journal of Bacteriology. US, vol. 178, No. 15, Aug. 1996, pp. 4704-4709, XP002239530, ISSN: 0021-9193, the whole document.
Gui L et al: "Autoregulation of iclR, the gene encoding the repressor of the glyoxylate bypass operon." Journal of Bacteriology. US, vol. 178, No. 1, Jan. 1996, pp. 321-324, XP002239531, ISSN: 0021-9193, the whole document.
Cortay J C et al: "Regulation of the acetate operon in *Escherichia coli*: purification and functional characterization of the IclR repressor." The EMBO Journal. England, vol. 10, No. 3, Mar. 1991, pp. 675-679, XP002239532, ISSN: 0261-4189, cited in the application, the whole document.
Donald L J et al: "Mass spectrometric study of the *Escherichia coli* repressor proteins, IclR and GclR, and their complexes with DNA." Protein Science: A Publication of the Protein Society. United States Jul. 2001, vol. 10, No. 7, Jul. 2001, pp. 1370-1380, XP008016713, ISSN: 0961-8368, the whole document.
Xu Y et al: "The FadR.DNA complex. Transcriptional control of fatty acid metabolism in *Escherichia coli*." The Journal of Biological Chemistry. US, vol. 276, No. 20, May 18, 2001 pp. 17373-17379, XP002247351, ISSN: 0021-9258, the whole document.
Farmer W R et al: "Reduction of aerobic acetate production by *Escherichia coli*." Applied and Environmental Microbiology. US, vol. 63, No. 8, Aug. 1997, pp. 3205-3210, XP002247352, ISSN:0099-2240, the whole document.
Dirusso C C et al: "Fatty acyl-coA binding domain of the transcription factor FadR. Characterization by deletion, affinity labeling, and isothermal titration calorimetry." The Journal of Biological Chemistry. US, vol. 273, No. 50, Dec. 11, 1998, pp. 33652-33659, XP002247353, ISSN: 0021-9258, the whole document.
Landgraf J R et al: "The Role of H-NS in One Carbon Metabolism" Biochimie, Masson, Paris, FR, vol. 76, No. 10/11, 1994, pp. 1063-1070, XP008014239, ISSN: 0300-9084, the whole document.

* cited by examiner

*Primary Examiner*—Robert B. Mondesi
*Assistant Examiner*—Kagnew Gebreyesus
(74) *Attorney, Agent, or Firm*—Oblon, Spivak, McClelland, Maier & Neustadt, P.C.

(57) ABSTRACT

This invention relates to a process for the production of L-amino acids, in particular L-threonine, in which the following steps are performed: a) fermentation of microorganisms of the Enterobacteriaceae family which produce the desired L-amino acid, in which at least one or more of the genes, selected from the group iclR and fadR, or nucleotide sequences coding therefor, are enhanced, in particular overexpressed, b) accumulation of the desired L-amino acid in the medium or in the cells of the bacteria and c) isolation of the desired L-amino acid.

19 Claims, 2 Drawing Sheets

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Synthetic DNA

<400> SEQUENCE: 1
```

```
gtccaacttt gtctagatga gttatgg                                                27

<210> SEQ ID NO 2
<211> LENGTH: 27
<212> TYPE: DNA
<213> ORGANISM: Artificial Sequence
<220> FEATURE:
<223> OTHER INFORMATION: Synthetic DNA

<400> SEQUENCE: 2
gaggggtttg aagcttaaac ggaaggg                                                27

<210> SEQ ID NO 3
<211> LENGTH: 28
<212> TYPE: DNA
<213> ORGANISM: Artificial Sequence
<220> FEATURE:
<223> OTHER INFORMATION: Synthetic DNA

<400> SEQUENCE: 3
cagttcagta tctagagcat gagctaac                                               28

<210> SEQ ID NO 4
<211> LENGTH: 28
<212> TYPE: DNA
<213> ORGANISM: Artificial Sequence
<220> FEATURE:
<223> OTHER INFORMATION: Synthetic DNA

<400> SEQUENCE: 4
ggtatgatgg gcagaagctt gcctctgc                                               28
```

PROCESS FOR THE PRODUCTION OF L-AMINO ACIDS USING STRAINS OF THE ENTEROBACTERIACEAE FAMILY WHICH CONTAIN AN ENHANCED FADR OR ICLR GENE

FIELD OF THE INVENTION

The present invention relates to a process for the production of L-amino acids, in particular L-threonine, using strains of the Enterobacteriaceae family, in which at least one or more genes, selected from the group iclR and fadR, is/are enhanced.

PRIOR ART

L-Amino acids, in particular L-threonine, are used in human medicine and in the pharmaceuticals industry, in the food industry and very particularly in animal nutrition.

It is known that L-amino acids are produced by fermentation of strains of Enterobacteriaceae, in particular *Escherichia coli* (*E. coli*) and *Serratia marcescens*. Due to their great significance, efforts are constantly being made to improve the production process. Improvements to the process may relate to measures concerning fermentation technology, such as for example stirring and oxygen supply, or to the composition of the nutrient media, such as for example sugar concentration during fermentation, or to working up to yield the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the threonine analogue α-amino-β-hydroxyvaleric acid (AHV), or are auxotrophic for regulatorily significant metabolites and produce L-amino acids, such as for example L-threonine.

For some years, methods of recombinant DNA technology have likewise been used to improve strains of the Enterobacteriaceae family which produce L-amino acids by amplifying individual amino acid biosynthesis genes and investigating the effect on production.

OBJECT OF THE INVENTION

The object of the invention is to provide novel measures for the improved fermentative production of L-amino acids, in particular L-threonine.

SUMMARY OF THE INVENTION

The invention provides a process for the fermentative production of L-amino acids, in particular L-threonine using microorganisms of the Enterobacteriaceae family, which in particular already produce L-amino acids and in which at least one or more of the nucleotide sequence(s) which code(s) for the genes iclR and fadR is/are enhanced.

DETAILED DESCRIPTION OF THE INVENTION

Figure 1:
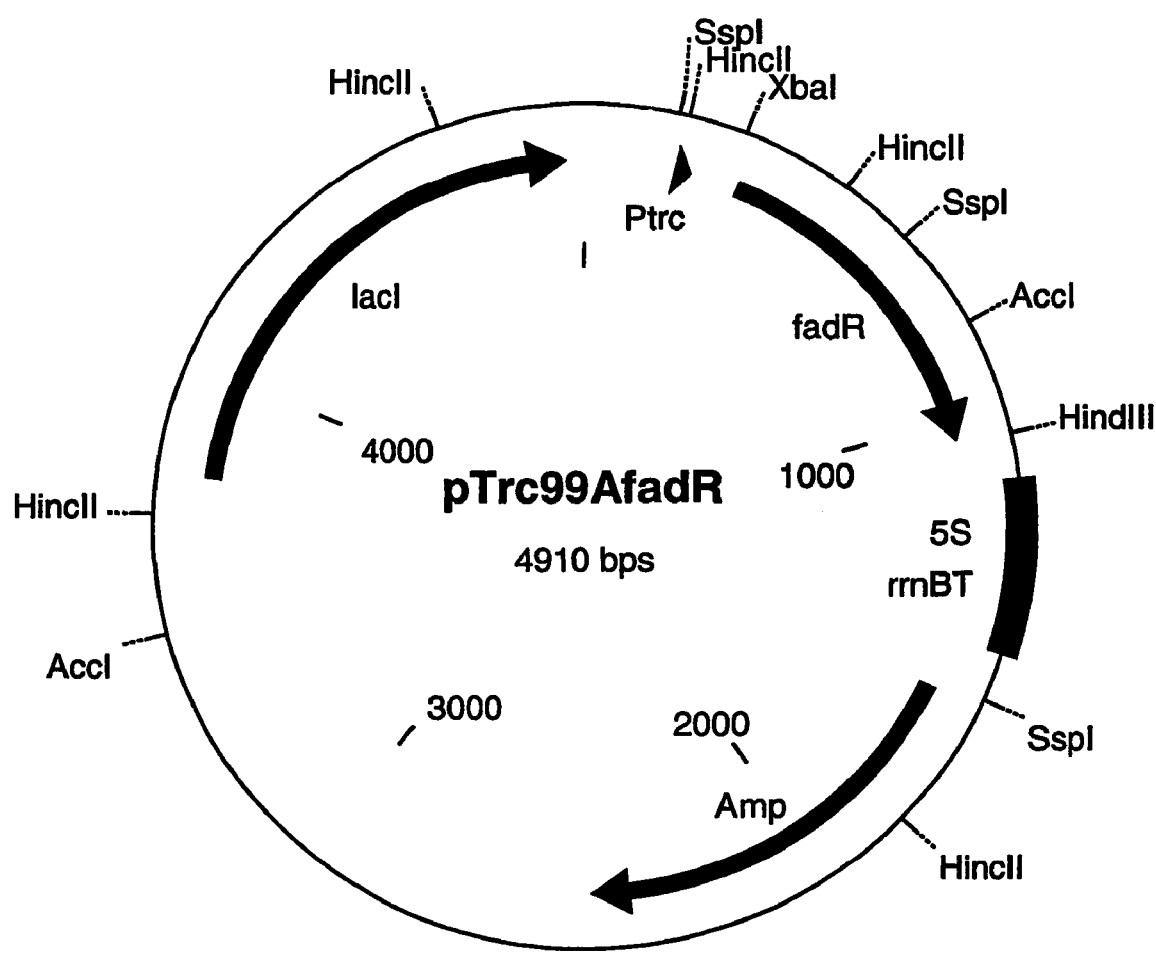
FIG. 1 depicts plasmid pTrc99AfadR.

Any subsequent mention of L-amino acids or amino acids should be taken to mean one or more amino acids, including the salts thereof, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-threonine is particularly preferred.

In this connection, the term "enhancement" describes the increase in the intracellular activity of one or more enzymes or proteins in a microorganism, which enzymes or proteins are coded by the corresponding DNA, for example by increasing the copy number of the gene or genes, by using a strong promoter or a gene or allele which codes for a corresponding enzyme or protein having elevated activity and optionally by combining these measures.

The enhancement, in particular overexpression, measures increase the activity or concentration of the corresponding protein in general by at least 10%, 25%, 50%, 75%, 100%, 150%, 200%, 300%, 400% or 500%, at most by 1000% or 2000%, relative to the activity or concentration of the wild type protein, or the activity or concentration of the protein in the starting microorganism.

The process is characterized in that the following steps are performed:

a) fermentation of microorganisms of the Enterobacteriaceae family, in which one or more of the genes, selected from the group iclR and fadR, or nucleotide sequences coding therefor, are enhanced, in particular overexpressed, b) accumulation of the corresponding L-amino acid in the medium or in the cells of the microorganisms of the Enterobacteriaceae family and c) isolation of the desired L-amino acid, wherein constituents of the fermentation broth and/or the biomass in their entirety or fractions thereof (>0 to 100%) optionally remain in the product.

The microorganisms provided by the present invention are capable of producing L-amino acids from glucose, sucrose, lactose, fructose, maltose, molasses, optionally starch, optionally cellulose or from glycerol and ethanol. They are representatives of the Enterobacteriaceae family selected from the genera *Escherichia, Erwinia, Providencia* and *Serratia*. The genera *Escherichia* and *Serratia* are preferred. Within the genus *Escherichia*, the species *Escherichia coli* may in particular be mentioned and, within the genus *Serratia*, the species *Serratia marcescens*. Suitable strains of the genus *Escherichia*, in particular L-threonine producing strains, in particular of the species *Escherichia coli* are for example

*Escherichia coli* TF427
*Escherichia coli* H4578
*Escherichia coli* KY10935
*Escherichia coli* VNIIgenetika MG442
*Escherichia coli* VNIIgenetika M1
*Escherichia coli* VNIIgenetika 472T23
*Escherichia coli* BKIIM B-3996
*Escherichia coli* kat 13
*Escherichia coli* KCCM-10132.

Suitable L-threonine producing strains of the genus *Serratia*, in particular of the species *Serratia marcescens* are for example

*Serratia marcescens* HNr21
*Serratia marcescens* TLr156
*Serratia marcescens* T2000.

L-Threonine producing strains from the Enterobacteriaceae family preferably have, inter alia, one or more of the genetic or phenotypic features selected from the group: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to rifampicin, resistance to valine analogues such as for example valine hydroxamate, resistance to purine analogues, such as for example 6-dimethylaminopurine, dependency on L-methionine, optionally partial and offsettable dependency on L-isoleucine, dependency on meso-diaminopimelic acid, auxotrophy with regard to threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optional ability to utilize sucrose, enhancement of the threonine operon, enhancement of homoserine dehydrogenase I-aspartate kinase I, preferably the feedback-resistant form, enhancement of homoserine kinase, enhancement of threonine synthase, enhancement of aspartate kinase, optionally the feedback-resistant form, enhancement of aspartate semialdehyde dehydrogenase, enhancement of phosphoenolpyruvate carboxylase, optionally the feedback-resistant form, enhancement of phosphoenolpyruvate synthase, enhancement of transhydrogenase, enhancement of the RhtB gene product, enhancement of the RhtC gene product, enhancement of YfiK gene product, enhancement of a pyruvate carboxylase, and attenuation of acetic acid formation.

It has been found that, after enhancement, in particular overexpression of at least one or more of the genes selected from the group iclR and fadR, microorganisms of the Enterobacteriaceae family produce L-amino acids, in particular L-threonine, in improved manner.

The nucleotide sequences of the genes of *Escherichia coli* are part of the prior art and may also be obtained by the genome sequence of *Escherichia coli* published by Blattner et al. (Science 277: 1453-1462 (1997)).

| iclR gene: | |
|---|---|
| Description: | Regulator of central intermediate metabolism, repressor of aceBAK operon (IclR) |
| Reference: | Sunnarborg et al.; Journal of Bacteriology 172(5): 2642-2649 (1990); Cortay et al.; EMBO Journal 10(3): 675-679 (1991) |
| Accession no.: | AE000475 |
| fadR gene: | |
| Description: | Regulator of fatty acid and acetate metabolism (FadR) |
| Reference: | DiRusso; Nucleic Acids Research 16 (16): 7995-8009 (1988); Raman et al.; Journal of Biological Chemistry 272(49): 30645-30650 (1997) |
| Accession no.: | AE000217 |
| Alternative gene names: | dec, ole, thdB |

SEQ ID NOS: 5 and 6 depict the polynucleotide and polypeptide sequences of iclR and the protein it encodes. SEQ ID NOS: 7 and 8 depict the polynucleotide and polypeptide sequences of the fadR gene and the polypeptide it encodes.

The nucleic acid sequences may be obtained from the databases of the National Center for Biotechnology Information (NCBI), the National Library of Medicine (Bethesda, Md., USA), the nucleotide sequence database of the European Molecular Biology Laboratories (EMBL, Heidelberg, Germany or Cambridge, UK) or the DNA Data Bank of Japan (DDBJ, Mishima, Japan).

The genes described in the stated references may be used according to the invention. Alleles of the genes arising from the degeneracy of the genetic code or from functionally neutral sense mutations may also be used.

Enhancement may be achieved, for example, by increasing gene expression or the catalytic properties of the proteins. Both measures may optionally be combined.

Overexpression may be achieved by increasing the copy number of the corresponding genes or by mutating the promoter and regulation region or the ribosome-binding site located upstream from the structural gene. Expression cassettes incorporated upstream from the structural gene act in the same manner. It is additionally possible to increase expression during fermentative L-threonine production by means of inducible promoters. Expression is also improved by measures to extend the lifetime of the mRNA. Enzyme activity is moreover enhanced by preventing degradation of the enzyme protein. The genes or gene constructs may either be present in plasmids in a variable copy number or be integrated in the chromosome and amplified. Alternatively, overexpression of the genes concerned may also be achieved by modifying the composition of the media and culture conditions.

The person skilled in the art will find guidance in this connection inter alia in Chang and Cohen (Journal of Bacteriology 134: 1141-1156 (1978)), in Hartley and Gregori (Gene 13: 347-353 (1981)), in Amann and Brosius (Gene 40: 183-190 (1985)), in de Broer et al. (Proceedings of the National Academy of Sciences of the United States of America 80: 21-25 (1983)), in LaVallie et al. (BIO/TECHNOLOGY 11: 187-193 (1993)), in PCT/US97/13359, in Llosa et al. (Plasmid 26: 222-224 (1991)), in Quandt and Klipp (Gene 80:161-169 (1989)), in Hamilton et al. (Journal of Bacteriology 171: 4617-4622 (1989)), in Jensen and Hammer (Biotechnology and Bioengineering 58: 191-195 (1998)) and in known textbooks of genetics and molecular biology.

Plasmid vectors replicable in Enterobacteriaceae, such as for example cloning vectors derived from pACYC184 (Bartolomé et al.; Gene 102: 75-78 (1991)), pTrc99A (Amann et al.; Gene 69: 301-315 (1988)) or pSC101 derivatives (Vocke and Bastia; Proceedings of the National Academy of Sciences of the United States of America 80 (21): 6557-6561 (1983)), may be used. A strain transformed with a plasmid vector may be used in a process according to the invention, wherein the plasmid vector bears at least one or more of the genes selected from the group iclR and fadR, or nucleotide sequences which code therefor.

It is also possible to introduce mutations which affect expression of the particular genes into various strains by sequence exchange (Hamilton et al.; Journal of Bacteriology 171: 4617-4622 (1989)), conjugation or transduction.

It may furthermore be advantageous for the production of L-amino acids, in particular L-threonine, with strains of the Enterobacteriaceae family, in addition to enhancing one or more of the genes selected from the group iclR and fadR, to enhance one or more enzymes of the known threonine biosynthetic pathway or enzymes of anaplerotic metabolism or enzymes for the production of reduced nicotinamide adenine dinucleotide phosphate or enzymes of glycolysis or PTS enzymes or enzymes of sulfur metabolism.

It is, for example, possible simultaneously to enhance, in particular overexpress, one or more of the genes selected from the group the thrABC operon, which codes for aspartate kinase, homoserine dehydrogenase, homoserine kinase and threonine synthase (U.S. Pat. No. 4,278,765), the pyc gene of *Corynebacterium glutamicum*, which codes for pyruvate carboxylase (WO 99/18228), the pps gene, which codes for phosphoenolpyruvate synthase (Molecular and General Genetics 231(2): 332-336 (1992)), the ppc gene, which codes for phosphoenolpyruvate carboxylase (Gene 31: 279-283 (1984)), the pntA and pntB genes, which code for transhydrogenase (European Journal of Biochemistry 158: 647-653 (1986)), the rhtB gene, which imparts homoserine resistance (EP-A-0 994 190), the mqo gene, which codes for malate:quinone oxidoreductase (Journal of Bacteriology 182: 6892-6899 (2000)), the rhtC gene, which imparts threonine resistance (EP-A-1 013 765), the thrE gene of *Corynebacterium glutamicum*, which codes for the threonine export protein (EP-A-1 085 091)

the gdhA gene, which codes for glutamate dehydrogenase (Nucleic Acids Research 11: 5257-5266 (1983); Gene 23: 199-209 (1983)), the hns gene, which codes for the DNA-binding protein HLP-II (Molecular and General Genetics 212: 199-202 (1988)), the pgm gene, which codes for phosphoglucomutase (Journal of Bacteriology 176: 5847-5851 (1994)), the fba gene, which codes for fructose biphosphate aldolase (Biochemical Journal 257: 529-534 (1989)), the ptsH gene of the ptsHIcrr operon which codes for the phosphohistidine protein hexose phosphotransferase of the phosphotransferase system, PTS (Journal of Biological Chemistry 262: 16241-16253 (1987)), the ptsI gene of the ptsHIcrr operon which codes for enzyme I of the phosphotransferase system, PTS (Journal of Biological Chemistry 262: 16241-16253 (1987)), the crr gene of the ptsHIcrr operon which codes for the glucose-specific IIA component of the phosphotransferase system, PTS (Journal of Biological Chemistry 262: 16241-16253 (1987)), the ptsG gene, which codes for the glucose-specific IIBC component (Journal of Biological Chemistry 261: 16398-16403 (1986)), the lrp gene, which codes for the regulator of the leucine regulon (Journal of Biological Chemistry 266: 10768-10774 (1991)), the mopB gene, which codes for the 10 kD chaperone (Journal of Biological Chemistry 261: 12414-12419 (1986)), which is also known by the name groES, the ahpC gene of the ahpCF operon which codes for the small subunit of alkyl hydroperoxide reductase (Proceedings of the National Academy of Sciences of the United States of America 92: 7617-7621 (1995)), the ahpF gene of the ahpCF operon which codes for the large subunit of alkyl hydroperoxide reductase (Proceedings of the National Academy of Sciences of the United States of America 92: 7617-7621 (1995)), the cysK gene, which codes for cysteine synthase A (Journal of Bacteriology 170: 3150-3157 (1988)), the cysB gene, which codes for the regulator of the cys regulon (Journal of Biological Chemistry 262: 5999-6005 (1987)), the cysJ gene of the cysJIH operon which codes for the flavoprotein of NADPH-sulfite reductase (Journal of Biological Chemistry 264: 15796-15808 (1989), Journal of Biological Chemistry 264: 15726-15737 (1989)), the cysI gene of the cysJIH operon which codes for the haemoprotein of NADPH-sulfite reductase (Journal of Biological Chemistry 264: 15796-15808 (1989), Journal of Biological Chemistry 264: 15726-15737 (1989)), the cysH gene of the cysJIH operon which codes for adenylyl sulfate reductase (Journal of Biological Chemistry 264: 15796-15808 (1989), Journal of Biological Chemistry 264: 15726-15737 (1989)), the phoB gene of the phoBR operon which codes for the positive regulator PhoB of the pho regulon (Journal of Molecular Biology 190 (1): 37-44 (1986)), the phoR gene of the phoBR operon which codes for the sensor protein of the pho regulon (Journal of Molecular Biology 192 (3): 549-556 (1986)), the phoE gene, which codes for protein E of the outer cell membrane (Journal of Molecular Biology 163 (4): 513-532 (1983)), the malE gene, which codes for the periplasmatic binding protein of maltose transport (Journal of Biological Chemistry 259 (16): 10606-10613 (1984)), the pykF gene, which codes for fructose-stimulated pyruvate kinase I (Journal of Bacteriology 177 (19): 5719-5722 (1995)), the pfkB gene, which codes for 6-phosphofructokinase II (Gene 28 (3): 337-342 (1984)), the talB gene, which codes for transaldolase B (Journal of Bacteriology 177 (20): 5930-5936 (1995)), the rseA gene of the rseABC operon which codes for a membrane protein with anti-sigmaE activity (Molecular Microbiology 24 (2): 355-371 (1997)), the rseC gene of the rseABC operon which codes for a global regulator of the sigmaE factor (Molecular Microbiology 24 (2): 355-371 (1997)), the sodA gene, which codes for superoxide dismutase (Journal of Bacteriology 155 (3): 1078-1087 (1983)), the sucA gene of the sucABCD operon which codes for the decarboxylase subunit of 2-ketoglutarate dehydrogenase (European Journal of Biochemistry 141 (2): 351-359 (1984)), the sucB gene of the sucABCD operon which codes for the dihydrolipoyltranssuccinase E2 subunit of 2-ketoglutarate dehydrogenase (European Journal of Biochemistry 141 (2): 361-374 (1984)), the sucC gene of the sucABCD operon which codes for the β-subunit of succinyl-CoA synthetase (Biochemistry 24 (22): 6245-6252 (1985)) and the sucD gene of the sucABCD operon which codes for the α-subunit of succinyl-CoA synthetase (Biochemistry 24 (22): 6245-6252 (1985)).

It may furthermore be advantageous for the production of L-amino acids, in particular L-threonine, in addition to enhancing one or more of the genes selected from the group iclR and fadR, to attenuate, in particular suppress or reduce the expression of, one or more genes selected from the group the tdh gene, which codes for threonine dehydrogenase (Journal of Bacteriology 169: 4716-4721 (1987)), the mdh gene, which codes for malate dehydrogenase (E.C. 1.1.1.37) (Archives in Microbiology 149: 36-42 (1987)), the yfjA gene product of the open reading frame (orf) (accession number AAC77180 of the National Center for Biotechnology Information (NCBI, Bethesda, Md., USA)), the ytfP gene product of the open reading frame (orf) (accession number AAC77179 of the National Center for Biotechnology Information (NCBI, Bethesda, Md., USA)), the pckA gene, which codes for the enzyme phosphoenolpyruvate carboxykinase (Journal of Bacteriology 172: 7151-7156 (1990)), the poxB gene, which codes for pyruvate oxidase (Nucleic Acids Research 14 (13): 5449-5460 (1986)), the aceA gene, which codes for the enzyme isocitrate lyase (Journal of Bacteriology 170: 4528-4536 (1988)), the dgsA gene, which codes for the DgsA regulator of the phosphotransferase system (Bioscience, Biotechnology and Biochemistry 59: 256-251 (1995)), which is also known by the name mlc gene, the fruR gene, which codes for the fructose repressor (Molecular and General Genetics 226: 332-336 (1991)), which is also known by the name cra gene, the rpoS gene which codes for the Sigma$^{38}$ factor (WO 01/05939), which is also known by the name katF gene, the aspA gene, which codes for aspartate ammonium lyase (aspartase) (Nucleic Acids Research 13(6): 2063-2074 (1985)) and the aceB gene, which codes for malate synthase A (Nucleic Acids Research 16(19): 9342 (1988)).

In this connection, the term "attenuation" means reducing or suppressing the intracellular activity of one or more enzymes (proteins) in a microorganism, which enzymes are coded by the corresponding DNA, for example by using a weak promoter or a gene or allele which codes for a corresponding enzyme which has a low activity or inactivates the corresponding enzyme (protein) or gene and optionally by combining these measures.

The attenuation measures reduce the activity or concentration of the corresponding protein in general to 0 to 75%, 0 to 50%, 0 to 25%, 0 to 10% or 0 to 5% of the activity or concentration of the wild type protein, or the activity or concentration of the protein in the starting microorganism.

It may furthermore be advantageous for the production of L-amino acids, in particular L-threonine, in addition to enhancing one or more of the genes selected from the group iclR and fadR, to suppress unwanted secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention may be cultured using the batch process, the fed batch process or repeated fed batch process. A summary of known culture methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must adequately satisfy the requirements of the particular strains. Culture media for various microorganisms are described in "Manual of Methods for General Bacteriology" from the American Society for Bacteriology (Washington D.C., USA, 1981).

Carbon sources which may be used include sugars and carbohydrates, such as for example glucose, sucrose, lactose, fructose, maltose, molasses, starch and optionally cellulose, oils and fats, such as for example soya oil, sunflower oil, peanut oil and coconut oil, fatty acids, such as for example palmitic acid, stearic acid and linoleic acid, alcohols, such as for example glycerol and ethanol, and organic acids, such as for example acetic acid. These substances may be used individually or as a mixture.

Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture.

Phosphorus sources which may be used are phosphoric acid, potassium dihydrogen phosphate or dipotassium hydrogen phosphate or the corresponding salts containing sodium. The culture medium must additionally contain salts of metals, such as magnesium sulfate or iron sulfate for example, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during culturing.

Basic compounds, such as sodium hydroxide, potassium hydroxide, ammonia or ammonia water, or acidic compounds, such as phosphoric acid or sulfuric acid, are used appropriately to control the pH of the culture. Foaming may be controlled by using antifoaming agents such as fatty acid polyglycol esters for example. Suitable selectively acting substances, such as for example antibiotics, may be added to the medium in order to maintain plasmid stability. Oxygen or gas mixtures containing oxygen, such as for example air, are introduced into the culture in order to maintain aerobic conditions. The temperature of the culture is normally from 25° C. to 45° C. and preferably from 30° C. to 40° C. The culture is continued until the maximum quantity of L-amino acids or L-threonine has formed. This aim is normally achieved within 10 to 160 hours.

Analysis of L-amino acids may be performed by anion exchange chromatography with subsequent ninhydrin derivation, as described in Spackman et al. (Analytical Chemistry, 30, 1190-1206 (1958)) or it may be performed by reversed phase HPLC, as described in Lindroth et al. (Analytical Chemistry 51: 1167-1174 (1979)).

The purpose of the process according to the invention is the fermentative production of L-amino acids, such as for example L-threonine, L-isoleucine, L-valine, L-methionine, L-homoserine and L-lysine, in particular L-threonine.

The present invention is illustrated in greater detail by the following practical examples.

The minimal medium (M9) and complete medium (LB) used for *Escherichia coli* are described by J. H. Miller (A Short Course in Bacterial Genetics (1992), Cold Spring Harbor Laboratory Press). Isolation of plasmid DNA from *Escherichia coli* and all restriction, ligation, Klenow and alkaline phosphatase treatment techniques were performed in accordance with Sambrook et al. (Molecular Cloning—A Laboratory Manual (1989) Cold Spring Harbor Laboratory Press). Unless otherwise stated, transformation of *Escherichia coli* was performed in accordance with Chung et al. (Proceedings of the National Academy of Sciences of the United States of America 86: 2172-2175 (1989)).

The incubation temperature during production of strains and transformants is 37° C.

EXAMPLE 1

Production of L-Threonine Using the fadR Gene

1a) Construction of pTrc99AfadR Expression Plasmid

The fadR gene from *E. coli* K12 is amplified using the polymerase chain reaction (PCR) and synthetic oligonucleotides. PCR primers are synthesized (MWG Biotech, Ebersberg, Germany) on the basis of the nucleotide sequence of the fadR gene in *E. coli* K12 MG1655 (accession no. AE000217, Blattner et al. (Science 277: 1453-1462 (1997)).

The primer sequences are modified in such a manner that recognition sites for restriction enzymes are obtained. The recognition sequence for XbaI is selected for the fadR3 primer, while the recognition sequence for HindIII is selected for the fadR4 primer, these sequences being indicated by the underlined portions of the nucleotide sequence shown below:

```
                                            (SEQ ID no. 1)
fadR3:  5' - GTCCAACTTTGTCTAGATGAGTTATGG - 3'

(SEQ ID no. 2)
fadR4:  5' - GAGGGGTTTGAAGCTTAAACGGAAGGG - 3'
```

The chromosomal *E. coli* K12 MG1655 DNA used for the PCR is isolated using "Qiagen Genomic-tips 100/G" (QIAGEN, Hilden, Germany) in accordance with the manufacturer's instructions. An approx. 800 bp DNA fragment can be amplified with the specific primers under standard PCR conditions (Innis et al. (1990) PCR Protocols. A Guide to Methods and Applications, Academic Press) using Pfu DNA polymerase (Promega Corporation, Madison, USA). The PCR product is ligated in accordance with the manufacturer's instructions with the vector pCR-Blunt II-TOPO (Zero Blunt TOPO PCR Cloning Kit, Invitrogen, Groningen, Netherlands) and transformed into *E. coli* strain TOP10. Plasmid-bearing cells are selected on LB agar which has been combined with 50 μg/ml of kanamycin. After isolation of the plasmid DNA, the vector pCR-Blunt II-TOPO-fadR is cleaved with the restriction enzymes HindIII and XbaI and, after separation, the fadR fragment is isolated in 0.8% agarose gel using the QIAquick Gel Extraction Kit (QIAGEN, Hilden, Germany). The vector pTrc99A (Pharmacia Biotech, Uppsala, Sweden) is cleaved with the enzymes HindIII and XbaI and ligated with the isolated fadR fragment. The *E. coli* strain XL1-Blue MRF' (Stratagene, La Jolla, USA) is transformed with the ligation batch and plasmid-bearing cells are selected on LB agar, which has been combined with 50 μg/ml of ampicillin. Success of the cloning can be verified after plasmid DNA isolation by performing a test cleavage with the enzymes AccI, HincII and SspI. The plasmid is designated pTrc99AfadR (FIG. 1).

1b) Production of L-Threonine with Strain MG442/pTrc99AfadR

The L-threonine-producing *E. coli* strain MG442 is described in patent U.S. Pat. No. 4,278,765 and has been deposited as CMIM B-1628 at the Russian National Collection of Industrial microorganisms (VKPM, Moscow, Russia).

Strain MG442 is transformed with the expression plasmid pTrc99AfadR described in Example 1a and the vector pTrc99A and plasmid-bearing cells are selected on LB agar with 50 μg/ml of ampicillin. In this manner, strains MG442/pTrc99AfadR and MG442/pTrc99A are obtained. Selected individual colonies are then further multiplied on minimal medium of the following composition: 3.5 g/l Na$_2$HPO$_4$*2H$_2$O, 1.5 g/l KH$_2$PO$_4$, 1 g/l NH$_4$Cl, 0.1 g/l MgSO$_4$*7H$_2$O, 2 g/l glucose, 20 g/l agar, 50 mg/l ampicillin. Formation of L-threonine is verified in 10 ml batch cultures in 100 ml Erlenmeyer flasks. Said culture is inoculated with 10 ml of preculture medium of the following composition: 2 g/l yeast extract, 10 g/l (NH$_4$)$_2$SO$_4$, 1 g/l KH$_2$PO$_4$, 0.5 g/l MgSO$_4$*7H$_2$O, 15 g/l CaCO$_3$, 20 g/l glucose, 50 mg/l ampicillin and incubated for 16 hours at 37° C. and 180 rpm in an ESR incubator from Kühner AG (Birsfelden, Switzerland).

250 μl portions of this preculture are transferred into 10 ml of production medium (25 g/l (NH$_4$)$_2$SO$_4$, 2 g/l KH$_2$PO$_4$, 1 g/l MgSO$_4$*7H$_2$O, 0.03 g/l FeSO$_4$*7H$_2$O, 0.018 g/l MnSO$_4$*1H$_2$O, 30 g/l CaCO$_3$, 20 g/l glucose, 50 mg/l ampicillin) and incubated for 48 hours at 37° C. Formation of L-threonine by the starting strain MG442 is verified in the same manner, but without the addition of ampicillin to the medium. After incubation, the optical density (OD) of the culture suspension is determined at a measurement wavelength of 660 nm using an LP2W photometer from the company Dr. Lange (Düsseldorf, Germany).

The concentration of L-threonine formed is then determined in the sterile-filtered culture supernatant using an amino acid analyzer from Eppendorf-BioTronik (Hamburg, Germany) by ion exchange chromatography and post-column reaction with ninhydrin detection.

Table 1 shows the result of the test.

TABLE 1

| Strain | OD (660 nm) | L-threonine g/l |
|---|---|---|
| MG442 | 5.6 | 1.4 |
| MG442/pTrc99A | 3.8 | 1.3 |
| MG442/pTrc99AfadR | 4.0 | 1.6 |

EXAMPLE 2

Production of L-Threonine Using the iclR Gene

2a) Construction of pTrc99AiclR Expression Plasmid

The iclR gene from *E. coli* K12 is amplified using the polymerase chain reaction (PCR) and synthetic oligonucleotides. PCR primers are synthesized (MWG Biotech, Ebersberg, Germany) on the basis of the nucleotide sequence of the iclR gene in *E. coli* K12 MG1655 (accession no. AE000475, Blattner et al. (Science 277: 1453-1462 (1997)). The primer sequences are modified in such a manner that recognition sites for restriction enzymes are obtained. The recognition sequence for XbaI is selected for the iclR3 primer, while the recognition sequence for HindIII is selected for the iclR4 primer, these sequences being indicated by the underlined portions of the nucleotide sequence shown below:

```
                                            (SEQ ID no. 3)
iclR3:  5' - CAGTTCAGTATCTAGAGCATGAGCTAAC - 3'

(SEQ ID no. 4)
iclR4:  5' - GGTATGATGGGCAGAAGCTTGCCTCTGC - 3'
```

The chromosomal *E. coli* K12 MG1655 DNA used for the PCR is isolated using "Qiagen Genomic-tips 100/G" (QIAGEN, Hilden, Germany) in accordance with the manufacturer's instructions. An approx. 950 bp DNA fragment can be amplified with the specific primers under standard PCR conditions (Innis et al. (1990) PCR Protocols. A Guide to Methods and Applications, Academic Press) using Pfu DNA polymerase (Promega Corporation, Madison, USA). The PCR product is ligated in accordance with the manufacturer's instructions with the vector pCR-Blunt II-TOPO (Zero Blunt TOPO PCR Cloning Kit, Invitrogen, Groningen, Netherlands) and transformed into *E. coli* strain TOP10.

Figure 2:
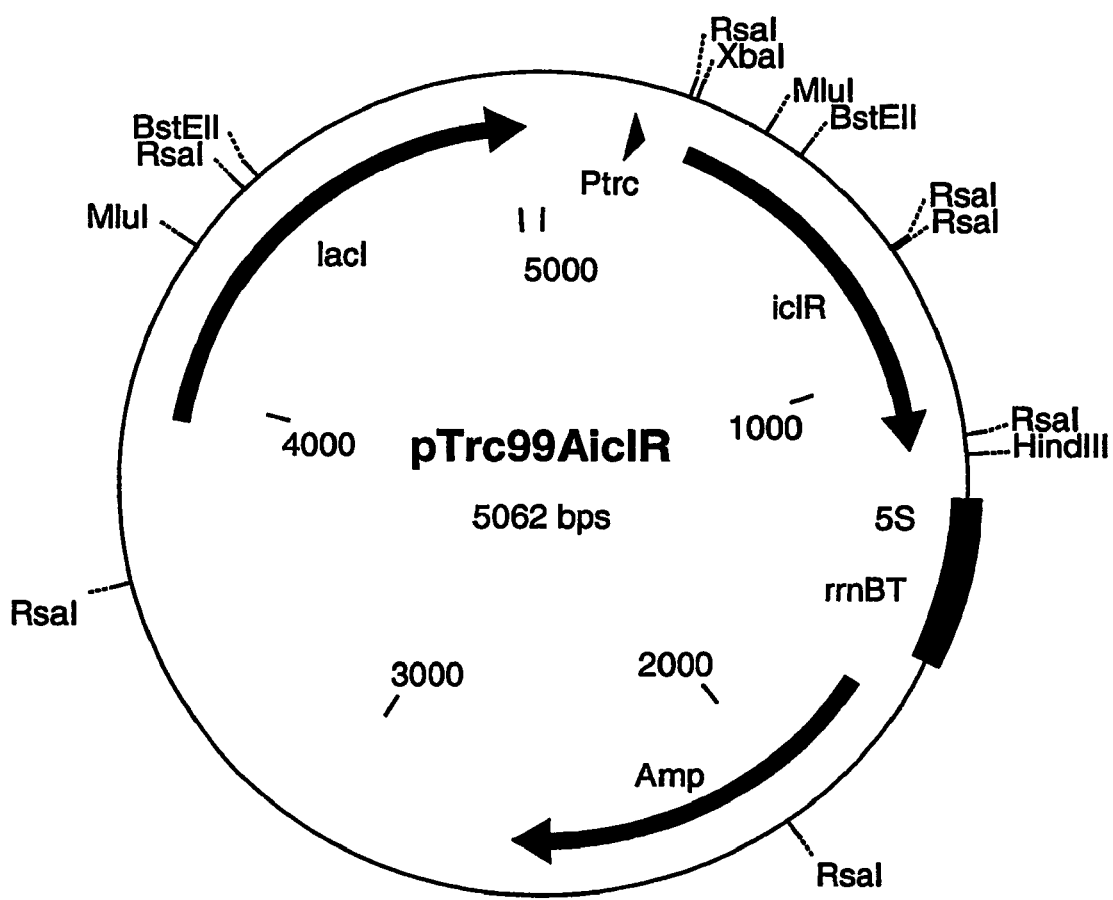
FIG. 2 depicts plasmid pTrc99AiclR.

Plasmid-bearing cells are selected on LB agar which has been combined with 50 μg/ml of kanamycin. After isolation of the plasmid DNA, the vector pCR-Blunt II-TOPO-iclR is cleaved with the restriction enzymes HindIII and XbaI and, after separation, the iclR fragment is isolated in 0.8% agarose gel using the QIAquick Gel Extraction Kit (QIAGEN, Hilden, Germany). The vector pTrc99A (Pharmacia Biotech, Uppsala, Sweden) is cleaved with the enzymes HindIII and XbaI and ligated with the isolated iclR fragment. The *E. coli* strain XL1-Blue MRF' (Stratagene, La Jolla, USA) is transformed with the ligation batch and plasmid-bearing cells are selected on LB agar, which has been combined with 50 μg/ml of ampicillin. Success of the cloning can be verified after plasmid DNA isolation by performing a test cleavage with the enzymes BstEII, MluI and RsaI. The plasmid is designated pTrc99AiclR (FIG. 2).

2b) Production of L-Threonine with Strain MG442/pTrc99Aic1R

The L-threonine-producing *E. coli* strain MG442 is described in patent U.S. Pat. No. 4,278,765 and has been deposited as CMIM B-1628 at the Russian National Collection of Industrial Microorganisms (VKPM, Moscow, Russia).

Strain MG442 is transformed with the expression plasmid pTrc99AiclR described in Example 2a and the vector pTrc99A and plasmid-bearing cells are selected on LB agar with 50 μg/ml of ampicillin. In this manner, strains MG442/pTrc99Aic1R and MG442/pTrc99A are obtained. Selected individual colonies are then further multiplied on minimal medium of the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar, 50 mg/l ampicillin. Formation of L-threonine is verified in 10 ml batch cultures in 100 ml Erlenmeyer flasks. Said culture is inoculated with 10 ml of preculture medium of the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, 50 mg/l ampicillin and incubated for 16 hours at 37° C. and 180 rpm in an ESR incubator from Kühner AG (Birsfelden, Switzerland).

250 μl portions of this preculture are transferred into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 30 g/l $CaCO_3$, 20 g/l glucose, 50 mg/l ampicillin) and incubated for 48 hours at 37° C. Formation of L-threonine by the starting strain MG442 is verified in the same manner, but without the addition of ampicillin to the medium. After incubation, the optical density (OD) of the culture suspension is determined at a measurement wavelength of 660 nm using an LP2W photometer from the company Dr. Lange (Düsseldorf, Germany).

The concentration of L-threonine formed is then determined in the sterile-filtered culture supernatant using an amino acid analyzer from Eppendorf-BioTronik (Hamburg, Germany) by ion exchange chromatography and post-column reaction with ninhydrin detection.

Table 2 shows the result of the test.

TABLE 2

| Strain | OD (660 nm) | L-threonine g/l |
| --- | --- | --- |
| MG442 | 5.6 | 1.4 |
| MG442/pTrc99A | 3.8 | 1.3 |
| MG442/pTrc99AiclR | 5.7 | 2.8 |

BRIEF DESCRIPTION OF THE FIGURES

FIG. 1: Map of plasmid pTrc99AfadR containing the fadR gene

FIG. 2: Map of plasmid pTrc99AiclR containing the iclR gene

The lengths stated should be considered to be approximate. The abbreviations and terms used have the following meaning:

Amp: ampicillin resistance gene
lacI: gene for the trc-promoter repressor protein
Ptrc: trc-promoter region, IPTG-inducible
fadR: coding region of the fadR gene
iclR: coding region of the iclR gene
5S: 5S rRNA region
rrnBT: rRNA terminator region The abbreviations for the restriction enzymes have the following meaning AccI: restriction endonuclease from *Acinetobacter calcoaceticus*
BstEII: restriction endonuclease from *Bacillus stearothermophilus* ATCC 12980
HincII: restriction endonuclease from *Haemophilus influenzae* Rc
HindIII: restriction endonuclease from *Haemophilus influenzae*
MluI: restriction endonuclease from *Micrococcus luteus* IFO 12992
RsaI: restriction endonuclease from *Rhodopseudomonas sphaeroides*
SspI: restriction endonuclease from *Sphaerotilus* species ATCC 13925
XbaI: restriction endonuclease from *Xanthomonas campestris*

What is claimed is:

1. A process for preparing an L-amino acid selected from the group consisting of L-threonine, L-lysine, and L-valine comprising:
    a) fermenting a suitable medium with a modified microorganism from the genus *Escherichia* which produces said L-amino acid, wherein said modified microorganism has been transformed with a vector that over-expresses the iclR gene and/or the fadR gene, compared to the corresponding untransformed *Escherichia* and wherein L-amino acid production in said modified *Escherichia* that over-expresses the iclR gene and/or the fadR gene is enhanced compared to the corresponding untransformed *Escherichia*; and
    b) recovering the L-amino acid;
    wherein the coding sequence of the iclR gene can be isolated from the DNA of an *Escherichia* by (PCR) and the primers iclR3 (SEQ ID NO: 3) and iclR4 (SEQ ID NO: 4), and
    wherein the coding sequence of the fadR gene can be isolated from the DNA of *Escherichia* using polymerase chain reaction (PCR) and the primers fadR3 (SEQ ID NO: 1) and fadR4 (SEQ ID NO: 2).

2. The process of claim 1, wherein the coding sequence of the iclR or the fadR gene, or both, can be isolated from *Escherichia coli*.

3. The process of claim 1, wherein said L-amino acid is L-lysine or L-threonine.

4. The process of claim 1, wherein said modified *Escherichia* is *Escherichia coli*.

5. The process of claim 1, wherein said modified *Escherichia* is at least one strain selected from the group of *Escherichia coli* strains consisting of TF427, H4578, KY10935, VNIIgenetika MG442, VNIIgenetika M1, VNIIgenetika 472T23, BKIIM B-3996, kat 13 and KCCM-10132.

6. The process of claim 1, wherein expression of the coding sequence of the iclR gene has been increased.

7. The process of claim 1, wherein expression of the coding sequence of the fadR gene has been increased.

8. The method of claim 1, wherein said modified *Escherichia* comprises at least one gene, which is over-expressed compared to the unmodified starting strain, selected from the group consisting of:
    the thrABC operon, which codes for aspartate kinase, homoserine dehydrogenase, homoserine kinase and threonine synthase,
    the pyc gene, which codes for pyruvate carboxylase,
    the pps gene, which codes for phosphoenolpyruvate synthase,
    the ppc gene, which codes for phosphoenolpyruvate carboxylase,
    the pntA and pntB genes, which code for transhydrogenase,
    the rhtB gene, which imparts homoserine resistance,
    the mqo gene, which codes for malate:quinone oxidoreductase,
    the rhtC gene, which imparts threonine resistance,
    the thrE gene, which codes for the threonine export protein,
    the gdhA gene, which codes for glutamate dehydrogenase,
    the hns gene, which codes for the DNA-binding protein HLP-II,
    the pgm gene, which codes for phosphoglucomutase,
    the fba gene, which codes for fructose biphosphate aldolase, the ptsH gene, which codes for phosphohistidine protein hexose phosphotransferase, the ptsI gene, which codes for enzyme I of the phosphotransferase system, the crr gene, which codes for the glucose-specific IIA component, the ptsG gene, which codes for the glucose-specific IIBC component, the lrp gene, which codes for the regulator of the leucine regulon, the mopB gene, which codes for the 10 kD chaperone, the ahpC gene, which codes for the small subunit of alkyl hydroperoxide reductase, the ahpF gene, which codes for the large subunit of alkyl hydroperoxide reductase, the cysK gene, which codes for cysteine synthase A, the cysB gene, which codes for the regulator of the cys regulon, the cysJ gene, which codes for the flavoprotein of NADPH-sulfite reductase, the cysI gene, which codes for the haemoprotein of NADPH-sulfite reductase, the cysH gene, which codes for adenylyl sulfate reductase, the phoB gene, which codes for the positive regulator PhoB of the pho regulon, the phoR gene, which codes for the sensor protein of the pho regulon, the phoE gene, which codes for protein E of the outer cell membrane, the malE gene, which codes for the periplasmatic binding protein of maltose transport, the pykF gene, which codes for fructose-stimulated pyruvate kinase I, the pfkB gene, which codes for 6-phosphofructokinase II, the talB gene, which codes for transaldolase B, the rseA gene, which codes for a membrane protein which acts as a negative regulator on sigmaE activity, the rseC gene, which codes for a global regulator of the sigmaE factor, the sodA gene, which codes for superoxide dismutase, the sucA gene, which codes for the decarboxylase subunit of 2-ketoglutarate dehydrogenase, the sucB gene, which codes for the dihydrolipoyltranssuccinase E2 subunit of 2-ketoglutarate dehydrogenase, the sucC gene, which codes for the β-subunit of succinyl-CoA synthetase and the sucD gene, which codes for the α-subunit of succinyl-CoA synthetase.

9. The method of claim 1, wherein said modified *Escherichia* comprises at least one gene, which is eliminated or attenuated compared to the unmodified starting strain, selected from the group consisting of:

the tdh gene, which codes for threonine dehydrogenase, the mdh gene, which codes for malate dehydrogenase, the polynucleotide encoding the yfjK gene product, the polynucleotide encoding the ytfP gene product, the pckA gene, which codes for phosphoenolpyruvate carboxykinase, the poxB gene, which codes for pyruvate oxidase, the aceA gene, which codes for isocitrate lyase, the dgsA gene, which codes for the DgsA regulator of the phosphotransferase system, the fruR gene, which codes for the fructose repressor, the rpoS gene which codes for the Sigma$^{38}$ factor, the aspA gene, which codes for aspartate ammonium lyase (aspartase) and the aceB gene, which codes for malate synthase A.

10. The process of claim 1, wherein said modified *Escherichia* ferments said medium until a maximum of said L-amino acid has formed.

11. The process of claim 1, wherein the L-amino acid is recovered from the culture medium after removal of 100% of the biomass.

12. The process of claim 1, wherein the L-amino acid is recovered from the culture medium after removal of less than 100% of the biomass, but more than 0% of the biomass.

13. The process of claim 1, wherein the L-amino acid is recovered from the biomass of said culture supernatant.

14. The process of claim 1, which is a batch process.

15. The process of claim 1, which is a fed batch or repeated fed batch process.

16. A process for preparing an L-amino acid selected from the group consisting of L-threonine, L-lysine, and L-valine comprising:

a) fermenting in a suitable medium a modified microorganism from the genus *Escherichia* which produces said L-amino acid, wherein said modified *Escherichia* has been transformed with a vector that over-expresses the iclR gene and/or the fadR gene, compared to the corresponding untransformed *Escherichia* and wherein L-amino acid production in said modified *Escherichia* that over-expresses the iclR gene and/or the fadR gene is enhanced compared to the corresponding untransformed *Escherichia*; and recovering the L-amino acid;

wherein the coding sequence of the iclR gene encodes a polypeptide comprising SEQ ID NO: 6 and the coding sequence of the fadR gene encodes a polypeptide comprising SEQ ID NO: 8.

17. A process for preparing L-threonine comprising:

a) fermenting a suitable medium with an L-threonine-producing *Escherichia* strain which has been modified to over-express the coding sequence of its iclR gene and/or its fadR gene, compared to the corresponding unmodified *Escherichia* coli strain, and which produces a greater amount of L-threonine compared to the corresponding unmodified *Escherichia* strain; and b) recovering the L-threonine;

wherein the coding sequence of the iclR gene can be isolated from the DNA of *Escherichia coli* by PCR using the primers iclR3 (SEQ ID NO: 3) and iclR4 (SEQ ID NO: 4), and wherein the coding sequence of the fadR gene can be isolated from the DNA of *Escherichia coli* by PCR using the primers fadR3 (SEQ ID NO: 1) and fadR4 (SEQ ID NO: 2).

18. A process for preparing L-lysine comprising:

a) fermenting a suitable medium with an L-lysine-producing *Escherichia* strain which has been modified to over-express the coding sequence of its iclR gene and/or its fadR gene, compared to the corresponding unmodified *Escherichia*, and which produces a greater amount of L-lysine compared to the corresponding unmodified *Escherichia* strain; and b) recovering the L-lysine;

wherein the coding sequence of the iclR gene can be isolated from the DNA of *Escherichia* by PCR using the primers iclR3 (SEQ ID NO: 3) and iclR4 (SEQ ID NO: 4), and wherein the coding sequence of the fadR gene can be isolated from the DNA of *Escherichia* by PCR using the primers fadR3 (SEQ ID NO: 1) and fadR4 (SEQ ID NO: 2).

19. A process for preparing L-valine comprising:

a) fermenting a suitable medium with an L-valine-producing *Escherichia* strain which has been modified to overexpress the coding sequence of its iclR gene and/or its fadR gene, compared to the corresponding unmodified *Escherichia*, and which produces a greater amount of L-valine compared to the corresponding unmodified *Escherichia* strain; and b) recovering the L-valine;

wherein the coding sequence of the iclR gene can be isolated from the DNA of *Escherichia* by PCR using the primers iclR3 (SEQ ID NO: 3) and iclR4 (SEQ ID NO: 4), and wherein the coding sequence of the fadR gene can be isolated from the DNA of *Escherichia* by PCR using the primers fadR3 (SEQ ID NO: 1) and fadR4 (SEQ ID NO: 2).

\* \* \* \* \*